United States Patent [19]

Shimizu et al.

[11] Patent Number: 5,378,773

[45] Date of Patent: Jan. 3, 1995

[54] PROCESS TO PREVENT SCALE ADHESION DURING POLYMERIZATION OF VINYL MONOMERS

[75] Inventors: Toshihide Shimizu, Urayasu; Mikio Watanabe, Kamisu, both of Japan

[73] Assignee: Shin-Etsu Chemical Co., Ltd., Tokyo, Japan

[21] Appl. No.: 70,994

[22] Filed: Jun. 4, 1993

[30] Foreign Application Priority Data

Jun. 4, 1992 [JP] Japan ................................ 4-170098
Jun. 4, 1992 [JP] Japan ................................ 4-170099
Aug. 28, 1992 [JP] Japan ................................ 4-253838

[51] Int. Cl.$^6$ ........................ C08F 2/16; C08F 114/06
[52] U.S. Cl. ........................... 526/62; 526/208; 526/217; 526/222; 526/234
[58] Field of Search ............... 526/62, 208, 217, 222, 526/234

[56] References Cited

U.S. PATENT DOCUMENTS

| | | | |
|---|---|---|---|
| 4,105,839 | 8/1978 | Koyanagi et al. | 526/62 |
| 4,220,743 | 9/1980 | Englin | 526/62 |
| 4,262,109 | 4/1981 | Englin et al. | 526/62 |
| 4,404,337 | 9/1983 | Hata et al. | 526/62 |
| 4,517,344 | 5/1985 | Mitani et al. | 526/62 |

FOREIGN PATENT DOCUMENTS 2383199 10/1978 France .

*Primary Examiner*—Joseph L. Schofer
*Assistant Examiner*—Tom Weber
*Attorney, Agent, or Firm*—Oblon, Spivak, McClelland, Maier, & Neustadt

[57] ABSTRACT

Aqueous polymerization of vinyl monomer is conducted in a vessel with an internal coating. This coating is composed of the condensation reaction of an aliphatic diamine and a quinone, with the addition of a reaction stopper when reaction is 70-99% complete. Reaction stopper is an inorganic compound of sodium or sulfur.

8 Claims, No Drawings

PROCESS TO PREVENT SCALE ADHESION DURING POLYMERIZATION OF VINYL MONOMERS

BACKGROUND OF THE INVENTION

1. Field of the Invention

The present invention relates to a polymer scale preventive agent useful in polymerization of a monomer having an ethylenically unsaturated double bond, a polymerization vessel effective in preventing polymer scale deposition, and a process of producing a polymer using said vessel.

2. Description of the Prior Art

As a method of polymerizing a monomer having an ethylenically unsaturated double bond, are known suspension polymerization, emulsion polymerization, solution polymerization, gas phase polymerization and bulk polymerization. In any type of the polymerizations, polymer scale is liable to be deposited on the areas with which the monomer come into contact during polymerization, such as inner walls, stirring equipment and so on of a polymerization vessel.

The deposition of the polymer scale on the inner wall results in disadvantages that the yield of the polymer and cooling capacity of the polymerization vessel are lowered; that the polymer scale may peel and mix into a polymeric product, thereby impairing the quality of thereof; and that removal of such polymer scale is laborious and hence time-consuming. Further, since the polymer scale contains unreacted monomers and operators may be exposed thereto, which may cause physical disorders in the operators.

Heretofore, as a method for preventing polymer scale deposition on the inner wall and so forth, methods by which a polymer scale preventive agent comprising an amine compound, quinone compound, aldehyde compound or the like is coated on the inner wall, etc. of a polymerization vessel or methods by which such compounds are added to an aqueous medium for polymerization (Japanese Patent Publication (KOKOKU) No. 45-30343 (1960)).

These methods can prevent the deposition of polymer scale if polymerization run is repeated within about 5 or 6 times; however, the number of repetition of polymerization run exceeds 5 or 6, the scale preventive effect is weakened. That is, the scale preventive effect is poor in durability. Particularly, the scale preventive effect is adversely affected where a water-soluble catalyst is used and unsatisfactory industrially.

It is proposed in Japanese Pre-examination Patent Publication (KOKAI) No. 60-30681 (1985) to form a coating of a condensation product of an aromatic amine compound and an aromatic nitro compound on the areas with which monomers come into contact, such as the inner wall of a polymerization vessel. The formation of the coating of such a condensation product enables repetition of about 100 to 200 polymerization runs without deposition of polymer scale on the areas in the liquid phase, i.e., under the liquid surface inside the polymerization vessel.

However, polymer scale deposition is liable to occur in the vicinity of the interface between the gas phase and the liquid phase which interface is located at the upper section of a polymerization vessel.

Once polymer scale is deposited in the vicinity of the interface between the gas phase and the liquid phase, the deposited scale will grow gradually as polymerization runs are repeated, and at last it is peeled from the inner wall, etc. and incorporated into the polymeric product. If the polymeric product containing the polymer scale is processed into formed products such as sheets or the like, the polymer scale causes increase in fish eyes in the formed products, lowering seriously the quality thereof.

Polymeric products obtained by polymerization are required to have a high whiteness. That is, when a polymeric product is formed into a sheet or the like without any addition of a coloring agent, the resulting formed product is more or less colored. Such coloration is called initial coloration, which is desired to be as low as possible. However, the coating comprising said condensation product of an aromatic amine compound and an aromatic nitro compound disclosed in the Japanese Preexamination Publication may be peeled or dissolved into a polymeric product, thereby lowering the whiteness or increasing the initial coloration thereof.

Furthermore, in forming a coating of the condensation product of the aromatic amine compound as described above, the condensation product is dissolved in a solvent to prepare a coating solution. The solvent is an organic solvent or a mixed solvent of water and an organic solvent, the mixed solvent being based on the organic solvent and normally containing the organic solvent in a concentration of 60% by weight or above. Therefore, there are the dangers of inflammation, explosion or the like due to the use of an organic solvent, together with safety problems in handling, such as toxicity.

SUMMARY OF THE INVENTION

It is accordingly an object of the present invention to provide a polymer scale preventive agent for use in polymerization of a monomer having an ethylenically unsaturated double bond that can prevent effectively the deposition of polymer scale not only in the areas in the liquid phase but also in the vicinity of the interface between the gas and liquid phases, and can produce polymeric products with a very small number of fish eyes and low initial coloration after processed into formed products such as sheets or the like, a polymerization vessel using the same, and a process of producing a polymer using the vessel.

In order to attain the above object, the present invention provides a polymer scale preventive agent for use in polymerization of a monomer having an ethylenically unsaturated double bond, comprising a condensation product obtained by condensing (A) an aliphatic diamine compound, and (B) a quinone compound in an aqueous medium.

Also, the present invention provides a polymerization vessel for polymerizing a monomer having an ethylenically unsaturated double bond, which polymerization vessel has, on its inner wall surface, a coating comprising a condensation product obtained by condensing (A) an aliphatic diamine compound, and (B) a quinone compound in an aqueous medium.

Further, the present invention provides a process of producing a polymer by polymerization of a monomer having an ethylenically unsaturated double bond in a polymerization vessel, comprising the step of carrying out the polymerization in a polymerization vessel having, on its inner wall surface, a coating comprising a condensation product obtained by condensing (A) an aliphatic diamine compound, and (B) a quinone compound in an aqueous medium, whereby polymer scale is prevented from being deposited.

According to the present invention, deposition of polymer scale can be effectively prevented not only on the areas in the liquid phase but also in the vicinity of the interface between the gas and liquid phases in a polymerization vessel. Therefore, the present invention makes it unnecessary to conduct the operation of removing the polymer scale after every polymerization run, and the productivity is thereby improved.

Further, when the polymeric product obtained by the application of the present invention is processed into formed products such as sheets, the resulting formed products have very few fish eyes.

Furthermore, the formed products obtained as above are low in initial coloration. That is, the formed products exhibit a luminosity index L in the Hunter's color difference equation described in JIS Z 8730(1980) of 70 or more in the case of vinyl chloride polymers and 80 or more in the case of SBR.

Moreover, the polymer scale preventive agents according to the present invention can be applied to inside wall surfaces of a polymerization vessel as a coating liquid to form a coating on the surfaces while using a reduced amount of organic solvent; therefore, the polymer scale preventive agents of the present invention are free from dangers of inflammation, explosion or the like and also from safety problems in handling, e.g., toxicity.

DETAILED DESCRIPTION OF PREFERRED EMBODIMENTS

The condensation product used as an essential constituent of the polymer scale preventive agent of the present invention is a compound which is obtained by condensing (A) an aliphatic diamine compound and (B) a quinone compound in an aqueous medium.

The starting materials and synthesis of the condensation product will now be described below.

(A) Aliphatic diamine compound

The aliphatic diamine compound (A) is an aliphatic organic compound having two primary amino groups (—$NH_2$), such as, for example, diaminoalkanes, diaminocycloalkanes, diaminodialkyl sulfides, piperazines and the like.

Among the diaminoalkanes for use as the aliphatic diamine compound (A), preferred are those having from 2 to 12 carbon atoms. Specific examples of such diaminoalkanes include 1,2-diaminoethane, 1,2-diaminopropane, 1,3-diaminopropane, 1,4-diaminobutane, 1,7-diaminoheptane, 1,6-diaminohexane, 1,8-diaminooctane, 9,10-diaminononane, 1,10-diaminodecane, 1,12-diaminododecane, 1,2-diamino-2-methylpropane, and the like. In each of these diaminoalkanes, at least one of the hydrogen atoms bonded to a carbon atom may have been substituted by a substituent group such as hydroxyl group or the like. Specific examples of such substituted diaminoalkanes include 1,3-diamino-2-hydroxypropane and the like.

Among the diaminocycloalkanes which can be used as the aliphatic diamine compound (A), preferred are those having from 3 to 8 carbon atoms, for example, 1,4-diaminocyclohexane, bis(4-aminocyclohexyl)methane and the like. In each of the usable diaminocycloalkanes, at least one of the hydrogen atoms bonded to a carbon atom may have been substituted by a substituent group such as hydroxyl group or the like. Specific examples of such substituted diaminocycloalkanes include 1,4-diamino-2-hydroxycyclohexane and so forth.

The diaminodialkyl sulfides for use as the aliphatic diamine compound (A) are compounds which have the general formula (1):

$$H_2N—C_mH_{2m}—S—C_nH_{2n}—NH_2 \qquad (1)$$

wherein m and n are the same as above. Specific examples of the diaminodialkyl sulfides include bis(3-aminopropyl) sulfide, bis(5-aminoheptyl) sulfide, and the like. sulfide, bis(5-aminoheptyl) sulfide, and the like.

Among the above-described aliphatic diamine compounds, preferred are 1,2-diaminoethane, 1,3-diaminopropane, 1,3-diamino-2-hydroxypropane, 1,4-diaminocyclohexane, bis(3-aminopropyl)methylamine, bis(3-aminopropyl) sulfide and piperazine.

The aliphatic diamine compounds as above may be used either singly or in combination of two or more.

(B) Quinone compound

The quinone compounds (B) include, for example, the compounds represented by the general formulas (2) to (5):

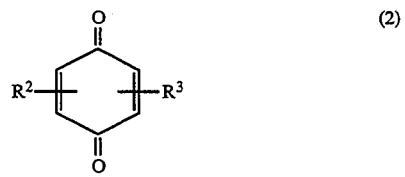

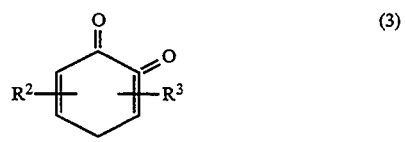

wherein in the formulas (2) and (3), $R^2$ is —H, —$NH_2$, —Cl, —Br, —OH, —$NO_2$, —$COCH_3$, —$OCH_3$, —$N(CH_3)_2$ or an alkyl group of from 1 to 3 carbon atoms, $R^3$ is —H, —$NH_2$, —OH, —$CH_3$, —COOH or —$SO_3H$.

Specifically, examples of the compounds of the general formula (2) or (3) include o-, m- and p-benzoquinones, hydroxy-p-benzoquinone, chloro-p-benzoquinone, bromo-p-benzoquinone, duroquinone, and chloranil.

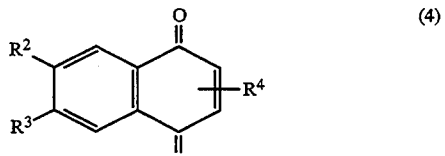

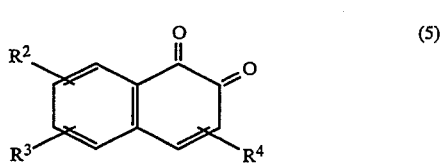

wherein in the formulas (4) and (5), $R^2$ and $R^3$ are as defined above, and $R^4$ is —H, —OH, —$CH_3$—Cl, —Br, —$COCH_3$, —$OCH_3$—COOH or —$SO_3H$.

Specifically, examples of the compounds of the general formula (4) or (5) include 6-methyl-1,4-naphthoquinone, 2-methyl-1,4-naphthoquinone, lawsone, juglone, plumbagin, α-naphthoquinone, and β-naphthoquinone.

Among the quinone compounds above, preferred are o-benzoquinone, p-benzoquinone, hydroxy-α-benzoquinone, duroquinone, lawsone, juglone, plumbagin, and α-naphthoquinone.

The quinone compounds may be used singly or in combination of two or more.

Condensation reaction

The condensation of the aliphatic diamine compound (A) and the quinone compound (B) is carried out in an aqueous medium, normally at a temperature ranging from room temperature to 100° C. for a period of from 0.1 to 300 hours, and preferably at a temperature in the range from room temperature to 50° C. for 0.5 to 100 hours.

As the medium for condensation reaction, an aqueous medium is used. The term "aqueous medium" used herein includes the meanings of water and of mixed solvents comprising water and an organic solvent miscible with water (in the mixed solvent, the proportion of the organic solvent is less than 70% by weight, preferably 50% by weight or less, more preferably 30% by weight or below). The organic solvents miscible with water include, for example, alcohols such as methanol, ethanol, propanol and the like; ketones such as acetone, methyl ethyl ketone and the like; and esters such as methyl acetate, ethyl acetate and the like.

The pH of the aqueous medium for the condensation reaction is preferably in the range from 7.5 to 13.5, more preferably from 9.0 to 13.0. Incidentally, the aliphatic diamine compounds (A) mostly are basic; in many cases, therefore, it is not particularly needed to adjust the pH of the aqueous medium for the reaction. Where pH adjustment is desired, a basic compound is used, for example, alkali metal compounds such as LiOH, KOH, NaOH, $Na_2CO_3$, $Na_2SiO_3$, $Na_2HOP_4$ and the like, and ammonium compounds such as $NH_4OH$ and the like.

Although the amounts of the aliphatic diamine compound (A) and the quinone compound (B) subjected to the condensation reaction depend on the kinds of the aliphatic diamine compound, quinone compound and solvent, reaction temperature, reaction time, etc., normally the quinone compound (B) is used preferably in an amount of from 0.05 to 20 parts by weight, more preferably from 0.1 to 5 parts by weight, per part by weight of the aliphatic diamine compound (A). If the amount of the quinone compound (B) is too large or too small relative to that of the aliphatic diamine compound (A), the resulting condensation product is poor in polymer scale preventing effect.

Where the condensation product obtained by condensing the components (A) and (B) in the aqueous medium has too high a degree of condensation, it may form sediment when used to prepare a coating liquid described later; in that case, the coating liquid obtained is not uniform, and the scale preventing effect is lowered. To avoid such a situation, therefore, it is preferable to add (C) a reaction stopper to the reaction mixture during the condensation of the components (A) and (B) in the aqueous medium, thereby controlling the degree of condensation of the condensation product.

(C) Reaction stopper

As the reaction stopper (C), for example, reducing agents may be used. The reducing agents usable include, for example, hydrogen, hydrogen iodide, hydrogen bromide, hydrogen sulfide, hydrides such as lithium aluminum hydride, sodium borohydride, calcium borohydride, zinc borohydride, tetraalkylammonium borohydride, trichlorosilane, triethylsilane, and the like; lower oxides or lower oxyacids such as carbon monoxide, sulfur dioxide, sodium thiosulfate, sodium thiosulfite, sodium sulfite, potassium sulfite, sodium bisulfite, and sodium hydrosulfite; sulfur compounds such as Rongalit, sodium sulfide, sodium polysulfide, and ammonium sulfide; alkali metals such as sodium and lithium; metals that are electrically highly positive such as magnesium, calcium, aluminum and zinc and their amalgams; salts of metals in a lower valence state such as iron(II) sulfate, tin(II) chloride, titanium(III) trichloride, and the like; phosphorus compounds such as phosphorus trichloride, phosphorus triiodide, trimethylphosphine, triphenylphosphine, trimethylphosphite, and hexamethylphosphorus triamide; hydrazine, diborane, and substituted diboranes such as ethane-1,2-diaminoborane, dimethylamine-borane, and pyridine-borane. Among these compounds, preferred are hydrogen iodide, hydrogen bromide, sodium borohydride, sulfur dioxide, sodium thiosulfate, sodium thiosulfite, sodium sulfite, potassium sulfite, sodium bisulfite and Rongalit.

These reaction stoppers may be used either singly or in combination of two or more.

The reaction stopper (C) may be added to the reaction mixture after the condensation reaction of the components (A) and (B) is initiated, and preferably the reaction stopper (C) is added to the reaction mixture just before a condensation product of the components (A) and (B) precipitates, that is, at the time when the condensation conversion of the components (A) and (B) has reached a value in the range of 70 to 99% by weight, particularly 80 to 98% by weight. When a reaction stopper is added to the reaction mixture, the condensation reaction is almost stopped. Nevertheless, after the addition of the reaction stopper (C), the reaction system is normally maintained at the reaction temperature under stirring for 2 to 50 hours, preferably for 5 to 20 hours.

Condensation conversion of the components (A) and (B) herein means the total amount in % by weight of the components (A) and (B) consumed for the condensation based on the total amount of the components (A) and (B) charged as monomers. That is, condensation conversion of the components (A) and (B) is defined by the equation:

Condensation conversion (% by weight)=$[(a-b)/a] \times 100$ wherein a stands for the total amount in part(s) by weight of the components (A) and (B) charged as monomers, and b stands for the total amount in part(s) by weight of the unreacted components (A) and (B).

It normally takes 0.2 to 100 hours for the condensation conversion of the components (A) and (B) to reach 70 to 99% by weight, although the time depends on the kinds of the components (A) and (B), etc.

Where the reaction stopper (C) is added to the reaction mixture, the preferred amount of the reaction stopper (C) is in the range of 0.005 to 5 parts by weight, more preferably 0.01 to 2 parts by weight per part by weight of the components (A) and (B) in total.

The polymer scale preventive agent according to the present invention, comprising the above-described condensation product as an indispensable constituent, is used to form, for example, a coating on the inner wall surface of a polymerization vessel, etc., whereby deposition of polymer scale on the inner wall surface, etc. is prevented. For forming the coating on the inner wall surface of a polymerization vessel, etc., normally, the polymer scale preventive agent is used in the form of a solution or a dispersed liquid, namely, in the form of a coating liquid.

Preparation of coating liquid

As the above-described coating liquid, for example, the solution containing the condensation product obtained upon the condensation reaction can be used, either directly as it is or after being diluted, for example, with an aqueous medium such as water.

As the medium for preparing the coating liquid, water or a mixed solvent comprising water and an organic solvent miscible with water can be used suitably. The organic solvents miscible with water include, for example, alcohols such as methanol, ethanol, propanol and the like; ketones such as acetone, methyl ethyl ketone and the like; and esters such as methyl acetate, ethyl acetate and the like. Where a mixed solvent comprising water and an organic solvent miscible with water is used, the proportion of the organic solvent is preferably set in a range such that there will be no dangers of inflammation, explosion or the like and that safety problems in handling, e.g., toxicity, will not be generated. Specifically, the preferred concentration of the organic solvent in the mixed solvent is 50% by weight or below, more preferably 30% by weight or below.

The concentration of the condensation product in the coating liquid is not particularly limited, so long as the total coating weight described later can be obtained. Normally, however, the concentration of the condensation product ranges from about 0.001 to about 15% by weight, and preferably from 0.01 to 1% by weight.

Besides, cationic, nonionic, anionic or other surface active agents and the like can be added to the coating liquid, provided the scale preventing effect is not thereby impaired. Further, if necessary, water-soluble polymeric compounds such as hydroxyl-containing polymeric compounds, cationic polymeric compounds, anionic polymeric compounds, amphoteric polymeric compounds and the like can also be added to the coating liquid as desired.

The hydroxyl-containing polymeric compounds include, for example, starches and their derivatives, such as amylose, amylopectin, dextrin, oxidized starch, acetylstarch, nitrostarch, methylstarch, carboxymethylstarch, etc.; hydroxyl-containing plant mucoids such as pectic acid, protopectic acid, pectinic acid, alginic acid, laminarin, fucoidin, agar-agar, carragheenin, etc.; hydroxyl-containing animal mucoids such as hyaluronic acid, chondroitin sulfuric acid, heparin, keratosulfuric acid, chitin, chitosan, charonin sulfuric acid, limacoitin sulfuric acid, etc.; nucleic acids such as ribonucleic acid, deoxyribonucleic acid, etc.; cellulose derivatives such as methyl cellulose, ethyl cellulose, carboxymethyl cellulose, glycol cellulose, benzyl cellulose, cyanoethyl cellulose, methylene ether of cellulose, triphenylmethyl cellulose, formyl cellulose, cellulose acetate, cellulose propionate, cellulose butyrate, cellulose acetate propionate, cellulose sulfate, cellulose carbamate, nitrocellulose, cellulose phosphate, cellulose xanthogenate, etc.; hemicelluloses such as alcohol lignin, dioxane lignin, phenol lignin, hydrotropic lignin, mercaptolignin, thioalkali lignin, acid lignin, cuproxam lignin, periodate lignin, etc.; phenol-formaldehyde resins; partially saponified polyvinyl alcohols; polyvinyl alcohols, and so forth.

The cationic polymeric compound includes cationic polymeric electrolytes containing a nitrogen atom with positive charge in the side chain, including, for example, polyvinylamines, polyethyleneamines, polyethyleneimines, polyacrylamides, N-vinyl-2-pyrrolidone/acrylamide copolymer, cyclic polymers of dimethyldiamylammonium chloride, cyclic polymers of dimethyldiethylammonium bromide, cyclic polymers of diallylamine hydrochloride, cyclic polymers of dimetyldiallylammonium chloride and sulfur dioxide, polyvinylpyridines, polyvinylpyrrolidones, polyvinylcarbazoles, polyvinylimidazolines, polydimethylaminoethyl acrylates, polydimethylaminoethyl methacrylates, polydiethylaminoethyl acrylate, and polydiethylaminoethyl methacrylate.

The anionic polymeric compound includes, for example, anionic polymeric compounds having a carboxyl group or sulfonic acid group in the side chain as exemplified by sulfomethylated compounds of polyacrylamide, polyacrylic acid, alginic acid, an acrylamide/vinylsulfonic acid copolymer, polymethacrylic acid and polystyrenesulfonic acid, and alkali metal salts or ammonium salts of these, and carboxymethyl cellulose.

The amphoteric polymeric compounds include, for example, glue, gelatin, casein, albumin and the like.

Furthermore, if necessary, inorganic compounds can also be added to the coating liquid as desired, provided the scale preventing effect is not thereby impaired. The inorganic compounds which can be added include, for example, silicic acids or silicates such as orthosilicic acid, metasilicic acid, mesodisilicic acid, mesotrisilicic acid, mesotetrasilicic acid, sodium metasilicate, water glass, etc.; metallic salts such as oxyacid salts, acetates, nitrate, hydroxides or halides of metal selected from alkaline earth metals such as magnesium, calcium and barium, zinc family group metals such as zinc, aluminum family metals such as aluminum, and platinum family metals such as platinum; inorganic colloids such as ferric hydroxide colloid, silicic acid colloid, barium sulfate colloid, aluminum hydroxide colloid, and the like. The inorganic colloids may be prepared, for example, by mechanical grinding, irradiation with ultrasonic wave, electrical dispersing techniques or chemical techniques.

Formation of the coating

The coating liquid prepared in the manner as above is applied to the inner walls of a polymerization vessel and then dried sufficiently at a temperature from room temperature to 100° C., for instance, followed by washing with water if necessary, to form the coating.

The coating liquid is preferably applied to not only the inner wall surfaces of a polymerization vessel but also other areas with which the monomer comes into contact during polymerization to form the coating on such areas. For example, on a stirring shaft, stirring blades, condensers, headers, search coil, bolts, nuts, etc.

More preferably, for formation of the coating, the coating liquid is applied to areas with which monomers do not come into contact during polymerization but on which polymer scale may deposit, for example, the areas with which unreacted monomers comes into contact of an unreacted monomer recovery system; specifically the inner surfaces, etc. of equipment and pipes of the recovery system. Specifically, such areas include the inner surfaces of monomer distillation columns, condensers, monomer stock tanks and valves.

The method of applying the scale preventing agent is not particularly limited, and includes, for example, the brush coating, spray coating, the method of filing the polymerization vessel with the coating liquid followed by withdrawal thereof, and automatic coating methods as disclosed in Japanese Pre-examination Patent Publication (KOKAI) Nos. 57-61001(1982) and 55-36288(1980), and Japanese Patent Publication (KOHYO) Nos. 56-501116(1981) and 56-501117(1981), and Japanese Pre-examination Publication (KOKAI) No. 59-11303(1984), etc.

The method of drying wet coated surfaces provided by application of the coating liquid, is not limited, either. Following methods can be used. That is, a method in which, after the coating liquid is applied, hot air with an suitable elevated temperature is blown to the coated surface, and a method in which the inner wall surface of a polymerization vessel and the surfaces of other parts to be coated are previously heated to from 30° to 80° C., and the coating liquid is directly applied to the heated inner wall surfaces, etc. After dried, the coated surfaces are washed with water if necessary.

The coating thus obtained normally has a coating weight of 0.001 g/m$^2$ to 5 g/m$^2$, and preferably from 0.05 to 2 g/m$^2$.

The coating operation may be conducted every one to ten-odd batches of polymerization. The formed coating has good durability and retains the scale-preventing action; therefore the coating operation may be performed every several batches of polymerization. Thus, the polymerization vessel can be used repeatedly without deposition of polymer scale, and productivity is improved.

Polymerization

After the formation of the coating on the inner wall surfaces of a polymerization vessel, and preferably also on other parts with which monomer may come into contact during polymerization, polymerization is carried out in accordance with conventional procedures. That is, a monomer having an ethylenically unsaturated double bond, a polymerization initiator, and optionally a polymerization medium such as water, etc., a suspending agent, a solid dispersing agent, a dispersing agent such as nonionic or anionic surfactants are charged into the polymerization vessel, followed by carrying out polymerization according to conventional methods.

The monomer having an ethylenically unsaturated double bond to which this invention can be applied may include, for example, vinyl halides such as vinyl chloride; vinyl esters such as vinyl acetate and vinyl propionate; acrylic acid, methacrylic acid, and esters or salts thereof; maleic acid, fumaric acid, and esters or salts thereof; and diene monomers such as butadiene, chloroprene and isoprene; styrene, acrylonitrile, vinylidene halides such as vinylidene chloride, and vinyl ethers. These may be used singly or in combination of two or more.

There are no particular restrictions on the type of polymerization to which this invention can be applied. The present invention is effective in any type of polymerization such as suspension polymerization, emulsion polymerization, solution polymerization, bulk polymerization, and gas phase polymerization. Particularly, the present invention is more suitable to polymerizations in an aqueous medium such as suspension or emulsion polymerization.

In the following, general conditions are described on each type of polymerizations.

In the case of suspension or emulsion polymerization, first, water and a dispersing agent are charged into a polymerization vessel, and thereafter a polymerization initiator is charged. Subsequently, the inside of the polymerization vessel is evacuated to a pressure of from 0.1 to 760 mmHg, and a monomer is then charged (whereupon the pressure inside the polymerization vessel usually becomes from 0.5 to 30 kgf/cm$^2$.G). Thereafter, polymerization is carried out at a temperature of from 30° to 150° C. During the polymerization, one or more of water, a dispersing agent and a polymerization initiator may be added, if necessary. Reaction temperature during the polymerization is different depending on the kind of monomer to be polymerized. For example, in the case of polymerizing vinyl chloride, polymerization is carried out at 30° to 80° C.; in the case of polymerizing styrene, polymerization is carried out at 50° to 150° C. The polymerization may be judged to be completed when the pressure inside the polymerization vessel falls to from 0 to 7 kgf/cm$^2$.G or when cooling water which passes through a jacket provided around the polymerization vessel indicates almost the same temperature at the inlet where it is charged and at the outlet where it is discharged (i.e., when liberation of heat due to polymerization reaction has subsided). The water, dispersing agent and polymerization initiator to be charged for polymerization are used in amounts of 20 to 500 parts by weight, 0.01 to 30 parts by weight, and 0.01 to 5 parts by weight, respectively, per 100 parts by weight of the monomer.

In the case of solution polymerization, an organic solvent such as toluene, xylene and pyridine is used as the polymerization medium in place of water. The dispersing agent is optionally used. The other conditions are generally the same as those described for suspension and emulsion polymerizations.

In the case of bulk polymerization, after the inside of a polymerization vessel is evacuated to a pressure of from about 0.01 mmHg to about 760 mmHg, a monomer and a polymerization initiator are charged into the polymerization vessel, and then polymerization is carried out at a temperature of from $-10°$ C. to 250° C. For example, in the case of polymerizing vinyl chloride, polymerization is carried out at 30° to 80° C.; in the case of polymerizing styrene, polymerization is carried out at 50° to 150° C.

The present invention makes it possible to prevent polymer scale from depositing, independent of materials constituting the inner wall, etc. of a polymerization vessel. For example, this invention can prevent deposition of polymer scale even in the case polymerization is carried out in a polymerization vessel made of a steel including stainless steel or lined with glass.

Any additive materials that have been conventionally added in a polymerization system can be used without any limitation. More specifically, this invention can effectively prevent polymers from depositing, even in polymerization systems containing the following additives: for example, polymerization initiators such as t-butyl peroxyneodecanoate, bis(2-ethylhexyl) peroxydicarbonate, 3,5,5-trimethylhexanoyl peroxide, α-cumyl peroxyneodecanoate, cumene hydroperoxide, cyclohexanone peroxide, t-butyl peroxypivalate, bis(2-ethoxyethyl) peroxydicarbonate, benzoyl peroxide, lauroyl peroxide, 2,4-dichlorobenzoyl peroxide, diisopropyl peroxydicarbonate, α,α'-azobisisobutyronitrile, α,α'-azobis-2,4-dimethylvaleronitrile, potassium peroxodisulfate, ammonium peroxodisulfate, and p-menthane hydroperoxide; suspension agents comprised of natural or synthetic polymeric compounds such as partially saponified polyvinyl alcohols, polyacrylic acids, vinyl acetate/maleic anhydride copolymers, cellulose derivatives such as hydroxypropyl methyl cellulose, and gelatin; solid dispersing agents such as calcium phosphate and hydroxyapatite; nonionic emulsifying agents such as sorbitan monolaurate, sorbitan trioleate and polyoxyethylene alkyl ether; anionic emulsifying agents such as sodium lauryl sulfate, sodium alkylbenzenesulfonates such as sodium dodecylbenzenesulfonate and sodium dioctylsulfosuccinate; fillers such as calcium carbonate and titanium oxide; stabilizers such as tribasic lead sulfate, calcium stearate, dibutyltin dilaurate and dioctyltin mercaptide; lubricants such as rice wax, stearic acid and cetyl alcohol; plasticizers such as DOP and DBP; chain transfer agents such as mercaptans such as t-dodecyl mercaptan, and trichloroethylene; and pH adjusters.

The polymer scale preventive agent of the present invention may be added to a polymerization mass in addition to the formation of the coating, so that the scale preventing effect is further improved. The amount of the polymer scale preventive agent to be added to the polymerization mass preferably in the range of about 10 to about 1,000 ppm based on the whole weight of the monomers charged. The addition should be conducted so that it may not adversely affect the quality of polymeric products to be obtained with respect to fish eyes, bulk density, particle size distribution, etc.

EXAMPLES

The working examples of the present invention and comparative examples will now be described below. In each table below, experiments marked with * are comparative examples and the other experiments are working examples of the present invention.

Production Example 1

Production of Condensation Product No.1

An autoclave was charged with 950 g of water and 25 g of p-benzoquinone as the quinone compound (B), and they were stirred at room temperature, so that the p-benzoquinone was dissolved in the water.

To the aqueous solution thus obtained, 25 g of 1,2-diaminoethane was added as the aliphatic diamine compound (A), and the reaction mixture obtained was heated to 25° C., and allowed to react at 25° C. for 3 hours. Thus, a solution of Condensation Product No. 1 was obtained.

Production of Condensation Product Nos. 2–20

In each production, the procedure of Production Condensation Product No. 1 was repeated, except for using an aliphatic diamine compound (A) and a quinone compound (B) given in Table 1 and a solvent given in Table 2 under conditions given in Table 2 (total concentration of (A)+(B), weight ratio (A):(B), reaction temperature and reaction time), and using a pH adjuster given in Table 2 for Condensation Product Nos. 6, 7, 9, 10, 15, 16, 17, 19 and 20 so as to control pH to the value given in Table 2. Thus, Condensation Product Nos. 2 to 20 were obtained.

TABLE 1

| Condensation product No. | (A) Aliphatic diamine compound | (B) Quinone compound |
|---|---|---|
| 1 | 1,2-Diaminoethane | p-Benzoquinone |
| 2* | 1,2-Diaminoethane | — |
| 3* | — | p-Benzoquinone |
| 4 | 1,2-Diaminoethane | Hydroxy-p-benzoquinone |
| 5 | 1,2-Diaminoethane | Duroquinone |
| 6 | 1,3-Diaminopropane | o-Benzoquinone |
| 7 | Piperazine | p-Benzoquinone |
| 8 | 1,2-Diaminoethane | Chloranil |
| 9 | 1,4-Diaminobutane | Chloro-p-benzoquinone |
| 10 | Piperazine | Duroquinone |
| 11 | 1,2-Diaminoethane | α-Naphthoquinone |
| 12* | 1,2-Diaminoethane | — |
| 13* | — | α-Naphthoquione |
| 14 | 1,2-Diaminoethane | Lawsone |
| 15 | 1,2-Diaminoethane | Juglone |
| 16 | 1,2-Diaminoethane | Plumbagin |
| 17 | 1,4-Diaminobutane | β-Naphthoquinone |
| 18 | Piperazine | α-Naphthoquinone |
| 19 | 1,3-Diaminopropane | 6-Methyl-1,4-Naphthoquinone |
| 20 | Piperazine | Lawsone |

TABLE 2

| Condensation product No. | Total conc. of (A) + (B) (wt. %) | (A):(B) (weight ratio) | pH Adjuster | pH | Solvent (weight ratio) | Reaction temp. (°C.) | Reaction time (Hr) |
|---|---|---|---|---|---|---|---|
| 1 | 5 | 100:100 | — | 11.2 | Water | 25 | 3 |
| 2* | 5 | — | — | 13.3 | Water | 25 | 3 |
| 3* | 5 | — | — | 6.0 | Water | 25 | 3 |
| 4 | 10 | 100:70 | — | 11.8 | Water | 30 | 5 |
| 5 | 2 | 100:30 | — | 11.0 | Water | 30 | 1 |
| 6 | 1 | 100:100 | NaOH | 12.0 | Water | 50 | 10 |
| 7 | 5 | 100:200 | NaOH | 11.5 | Water:Methanol (90:10) | 60 | 15 |
| 8 | 5 | 100:20 | — | 11.9 | Water | 40 | 5 |
| 9 | 5 | 100:50 | KOH | 11.5 | Water | 20 | 15 |
| 10 | 2 | 100:50 | NaOH | 13.0 | Water:Acetone (90:10) | 80 | 10 |
| 11 | 2 | 100:100 | — | 11.2 | Water | 25 | 10 |
| 12* | 2 | — | — | 12.3 | Water | 25 | 10 |
| 13* | 2 | — | — | 6.1 | Water | 25 | 10 |
| 14 | 2 | 100:200 | — | 11.1 | Water | 40 | 5 |
| 15 | 3 | 100:50 | NaOH | 12.0 | Water | 100 | 5 |
| 16 | 2 | 100:50 | KOH | 12.5 | Water:Methanol (90:10) | 70 | 5 |

TABLE 2-continued

| Condensation product No. | Total conc. of (A) + (B) (wt. %) | (A):(B) (weight ratio) | pH Adjuster | pH | Solvent (weight ratio) | Reaction temp. (°C.) | Reaction time (Hr) |
|---|---|---|---|---|---|---|---|
| 17 | 1 | 100:10 | KOH | 10.5 | water:Methanol (80:20) | 50 | 1 |
| 18 | 5 | 100:30 | — | 11.6 | Water | 40 | 15 |
| 19 | 2 | 100:20 | KOH | 11.0 | Water:Acetone (90:10) | 30 | 20 |
| 20 | 2 | 100:200 | NaOH | 12.0 | Water | 20 | 10 |

Example 1 (Experiment Nos. 101 to 120)

In each experiment, polymerization was conducted using a stainless steel polymerization vessel with an inner capacity of 1,000 liters and having a stirrer, as described below.

First, a coating liquid as shown in Table 3 (solvent composition, and concentration of condensation product) was prepared using a condensation product and a solvent given in Table 3. The coating liquid was applied to the inner wall, the stirring shaft, the stirring blades and other areas with which a monomer comes into contact of the polymerization vessel. The applied coating liquid was dried by heating at 40° C. for 15 minutes to form a coating, which was then washed with water.

Thereafter, into the polymerization vessel in which the coating was formed as above, 400 kg of water, 200 kg of vinyl chloride, 250 g of a partially saponified polyvinyl alcohol, 25 g of hydroxypropyl methyl cellulose and 70 g of 3,5,5-trimethylhexanoyl peroxide were charged, followed by polymerization at 66° C. for 6 hours. After the completion of the polymerization, the produced polymer was taken out and unreacted monomer was recovered out of the polymerization vessel. Subsequently, the inside of the polymerization vessel was washed with water and residual resin was removed.

The batch above comprising the operations of polymerization and washing with water, but not including the coating operation, was repeated the number of times shown in Table 4. After the final batch was over, the amount of polymer scale deposited on an area located in the liquid phase and on an area in the vicinity of the interface between the gas and liquid phases in the polymerization vessel, was measured according to the method below.

Measurement of the amount of polymer scale

The scale deposited in an area of 10 cm square on the inner wall is scraped off with a stainless steel spatula as completely as possible to be confirmed with naked eyes, and then the scraped scale is weighed on a balance. Thereafter, the amount of the deposited scale per area of 1 m$^2$ is obtained by multiplying the measured value by 100.

The number of fish eyes which may appear when a polymer is formed into sheet was measured with respect to the polymers produced in the experiments according to the method below.

Measurement of fish eyes

A hundred parts by weight of a polymer, 50 parts by weight of dioctyl phthalate (DOP), 1 part by weight of dibutyltin dilaurate, 1 part by weight of cetyl alcohol, 0.25 part by weight of titanium oxide and 0.05 part by weight of carbon black are formulated to prepare a mixture. The mixture is kneaded at 150° C. for 7 minutes with 6 inch rolls, and then formed into a sheet 0.2 mm thick. The sheet is examined for the number of fish eyes per 100 cm$^2$ by light transmission.

Further, to evaluate initial coloration at the time a polymer is formed into sheet, luminosity index L was measured according to the method below.

Measurement of luminosity index L

A hundred parts by weight of a polymer, 1 part by weight of a tin laurate stabilizing agent (trade name: TS-101, product of Akisima Chemical Co.) and 0.5 part by weight of cadmium stabilizing agent (trade name: C-100J, product of Katsuta Kako Co.), and 50 parts by weight of DOP are kneaded at 160° C. for 5 minutes with a twin roll mill, and then formed into a sheet 1 mm thick. Subsequently, this sheet is placed in a mold measuring 4 cm×4×1.5 cm (depth), is heated at 160° C. and a pressure of 65 to 70 kgf/cm$^2$ for 0.2 hour and press molded under the same conditions to prepare a test specimen. This test specimen is measured for luminosity index L in the Hunter's color difference equation described in JIS Z 8730 (1980). The higher the value of L of the test specimen, the higher the whiteness (namely, the lower the initial coloration) of the polymer.

The value of L was determined as follows. The stimulus value Y of XYZ color system is determined according to the photoelectric tristimulus colorimetry using the standard light C, photoelectric colorimeter (Color measuring color difference meter Model Z-1001DP, product of Nippon Denshoku Kogyo K.K.) in accordance with JIS Z 8722. As the geometric condition for illumination and being illuminated, the condition d defined in section 4.3.1 of JIS Z 8722 is adopted. Next, L is calculated based on the equation: $L = 10Y^{\frac{1}{2}}$ described in JIS Z 8730 (1980).

The results of the above measurements are given in Table 4.

TABLE 3

| | Coating liquid | | |
|---|---|---|---|
| Exp. No. | Condensation product No. | Concentration (wt. %) | Solvent (weight ratio) |
| 101 | 1 | 0.2 | Water:Methanol (95:5) |
| 102* | 2 | 0.2 | Water:Methanol (95:5) |
| 103* | 3 | 0.2 | Water:Methanol (95:5) |
| 104 | 4 | 0.2 | Water |
| 105 | 5 | 0.2 | Water |
| 106 | 6 | 0.1 | Water |
| 107 | 7 | 0.3 | Water:Methanol (90:10) |
| 108 | 8 | 0.3 | Water:Methanol (90:10) |
| 109 | 9 | 0.2 | Water:Methanol (95:5) |
| 110 | 10 | 0.2 | Water:Acetone (90:10) |
| 111 | 11 | 0.2 | Water |
| 112* | 12* | 0.2 | Water |
| 113* | 13* | 0.2 | Water |
| 114 | 14 | 0.2 | Water |
| 115 | 15 | 0.1 | Water |
| 116 | 16 | 0.3 | Water:Methanol (90:10) |
| 117 | 17 | 0.5 | Water:Methanol (85:15) |
| 118 | 18 | 0.2 | Water:Methanol (95:5) |
| 119 | 19 | 0.2 | Water:Acetone (95:5) |

TABLE 3-continued

| Exp. No. | Coating liquid | | |
|---|---|---|---|
| | Condensation product No. | Concentration (wt. %) | Solvent (weight ratio) |
| 120 | 20 | 0.2 | Water |

TABLE 4

| Exp. No. | Repetition number of batch (batches) | Results of polymerization | | | |
|---|---|---|---|---|---|
| | | Polymer scale amount (g/m$^2$) | | Number of fish eyes | Luminosity index (L) |
| | | Liquid phase | Around interface of gas and liquid phases | | |
| 101 | 5 | 0 | 72 | 18 | 73.0 |
| 102* | 2 | 1100 | 2600 | 36 | 72.5 |
| 103* | 2 | 87 | 310 | 26 | 72.5 |
| 104 | 5 | 0 | 81 | 18 | 73.0 |
| 105 | 5 | 0 | 79 | 18 | 73.0 |
| 106 | 5 | 1 | 96 | 21 | 73.0 |
| 107 | 5 | 0 | 82 | 19 | 73.0 |
| 108 | 5 | 0 | 76 | 18 | 73.0 |
| 109 | 5 | 1 | 104 | 25 | 73.0 |
| 110 | 5 | 0 | 77 | 19 | 73.0 |
| 112* | 2 | 1100 | 2600 | 36 | 72.5 |
| 113* | 2 | 22 | 230 | 25 | 72.5 |
| 114 | 5 | 0 | 45 | 13 | 73.0 |
| 115 | 5 | 0 | 78 | 18 | 73.0 |
| 116 | 5 | 0 | 48 | 14 | 73.0 |
| 117 | 5 | 0 | 51 | 14 | 73.0 |
| 118 | 5 | 0 | 50 | 15 | 73.0 |
| 119 | 5 | 0 | 47 | 14 | 73.0 |
| 120 | 5 | 0 | 44 | 14 | 73.0 |

Example 2 (Experiment Nos. 201 to 216)

In each experiment, polymerization was conducted using a stainless steel polymerization vessel with an inner capacity of 20 liters and having a stirrer, as described below.

First, a coating liquid as shown in Table 5 (solvent composition, and concentration of condensation product) was prepared using a condensation product and solvent given in Table 5. The coating liquid was applied to the inner wall, the stirring shaft, the stirring blades and other areas with which a monomer comes into contact of the polymerization vessel. The applied coating liquid was dried by heating at 50° C. for 15 minutes to form a coating, which was then washed with water.

Thereafter, into the polymerization vessel in which the coating was formed as above, 9 kg of water, 225 g of sodium dodecylbenzenesulfonate, 12 g of t-dodecyl mercaptan and 13 g of potassium peroxodisulfate were charged. After the inside of the polymerization vessel was replaced with a nitrogen gas, 1.3 kg of styrene and 3.8 kg of butadiene were charged, followed by polymerization at 50° C. for 20 hours. After the completion of the polymerization, the produced polymer was taken out and unreacted monomer was recovered out of the polymerization vessel. Subsequently, the inside of the polymerization vessel was washed with water and residual resin was removed.

The batch above comprising the operations of polymerization and washing with water, but not including the coating operation, was repeated the number of times shown in Table 6. After the final batch was over, the amount of polymer scale deposited on an area located in the liquid phase and on an area in the vicinity of the interface between the gas and liquid phases in the polymerization vessel, was measured in the same manner as in Example 1.

Measurement of luminosity index L

To 1 kg of a polymer latex obtained was added 1 kg of 2% magnesium sulfate solution to cause aggregation and sedimentation. The sediment was filtered off, washed with a hot water at 80° to 90° C. twice or three times and dried at 40° C. for 25 hours in a vacuum dryer to give a resin. The resin was placed in a mold measuring 9×9×0.1 cm (depth), heated at 195° C. under a pressure of 50 to 60 kgf/cm$^2$ for 0.2 hour and press molded under the final pressure of 80 kgf/cm$^2$ to prepare a test specimen. This test specimen was measured for luminosity index L in the same manner as in Example 1.

The results of the above measurements are given in Table 6.

TABLE 5

| Exp. No. | Coating liquid | | |
|---|---|---|---|
| | Condensation product No. | Concentration (wt. %) | Solvent (weight ratio) |
| 201 | 1 | 0.2 | Water:Methanol (95:5) |
| 202* | 2 | 0.2 | Water:Methanol (95:5) |
| 203* | 3 | 0.2 | Water:Methanol (95:5) |
| 204 | 4 | 0.2 | Water |
| 205 | 5 | 0.2 | Water |
| 206 | 7 | 0.3 | Water:Methanol (90:10) |
| 207 | 8 | 0.3 | Water |
| 208 | 10 | 0.2 | Water:Acetone (90:10) |
| 209 | 11 | 0.2 | Water |
| 210* | 12* | 0.2 | Water |
| 211* | 13* | 0.2 | Water |
| 212 | 14 | 0.2 | Water |
| 213 | 16 | 0.3 | Water:Methanol (90:10) |
| 214 | 18 | 0.2 | Water:Methanol (90:10) |
| 215 | 19 | 0.2 | Water:Methanol (90:10) |
| 216 | 20 | 0.2 | Water:Methanol (90:10) |

TABLE 6

| Exp. No. | Repetition number of batch (batches) | Results of polymerization | | |
|---|---|---|---|---|
| | | Polymer scale amount (g/m$^2$) | | Luminosity index (L) |
| | | Liquid phase | Around interface of gas and liquid phases | |
| 201 | 3 | 0 | 73 | 85.0 |
| 202* | 2 | 280 | 620 | 84.5 |
| 203* | 2 | 210 | 560 | 84.5 |

TABLE 6-continued

| Exp. No. | Repetition number of batch (batches) | Results of polymerization | | |
|---|---|---|---|---|
| | | Polymer scale amount (g/m²) | | Luminosity index (L) |
| | | Liquid phase | Around interface of gas and liquid phases | |
| 204 | 3 | 0 | 85 | 85.0 |
| 205 | 3 | 0 | 91 | 85.0 |
| 206 | 3 | 0 | 96 | 85.0 |
| 207 | 3 | 0 | 87 | 85.0 |
| 208 | 3 | 0 | 82 | 85.0 |
| 209 | 3 | 0 | 42 | 85.0 |
| 210* | 2 | 280 | 620 | 84.5 |
| 211* | 2 | 170 | 430 | 84.5 |
| 212 | 3 | 0 | 57 | 85.0 |
| 213 | 3 | 0 | 46 | 85.0 |
| 214 | 3 | 0 | 52 | 85.0 |
| 215 | 3 | 0 | 50 | 85.0 |
| 216 | 3 | 0 | 24 | 85.0 |

Production Example 2

Production of Condensation Product No. 21

An autoclave was charged with 882 g of water and 4 g of 1,2-diaminoethane as the aliphatic diamine compound (A), and they were stirred at room temperature, so that the 1,2-diaminoethane was dissolved in the water.

To the aqueous solution thus obtained, 2 g of α-naphthoquinone was as the quinone compound (B), and the mixture obtained was allowed to react at room temperature for 10 hours. Then, 1 g of sodium hydrosulfite as the reaction stopper (C) dissolved in 98 g of water was added to the reaction mixture. The condensation conversion of the aliphatic diamine compound and the quinone compound at the time when the reaction stopper (C) began to be added, was measured in accordance with the method below and found to be 95% by weight.

The solution to which the reaction stopper was added as mentioned above was stirred for another 0.5 hour and then cooled to give the solution of Condensation Product No. 21.

Measurement of condensation conversion

The unreacted aliphatic diamine compound (i.e., 1,2-diaminoethane in Condensation Product No. 21) and quinone compound (i.e., α-naphthoquinone) in a reaction mixture is determined by liquid chromatography.

The condensation conversion is calculated by the equation:

$$\text{Condensation conversion}(\% \text{ by weight}) = [(a-b)/a] \times 100$$

wherein a stands for the total amount of the aliphatic diamine compound and quinone compound charged and b stands for the amount of the unreacted aliphatic diamine compound and quinone compound determined as above.

Production of Condensation Product Nos. 22-29

In each production, the procedure of Production Condensation Product No. 21 was repeated, except for using an aliphatic diamine compound (A), quinone compound (B), reaction stopper (C) and solvent given in Table 7 under conditions given in Table 8. The conditions include the total concentration of (A)+(B), weight ratio (A):(B), pH, reaction temperature, the amount of the component (C) relative to the total amount of (A)+(B) (added amount of (C)), elapsed time from the start of the condensation of the components (A) and (B) until the component began to be added (hereinafter referred to "elapsed time till addition of (C)"), condensation conversion of the components (A) and (B) at the time when the component (C) began to be added, and stirring time after the addition of the components (C).

TABLE 7

| Condensation product No. | (A) Aliphatic diamine compound | (B) Quinone compound | (C) Reaction stopper | Solvent (weight ratio) |
|---|---|---|---|---|
| 21 | 1,2-Diaminoethane | α-Naphthoquinone | Sodium Hydrosulfite | Water |
| 22 | 1,2-Diaminoethane | p-Benzoquinone | Sodium hydrosulfite | Water |
| 23 | 1,2-Diaminoethane | p-Benzoquinone | Sulfur dioxide | Water |
| 24 | 1,2-Diaminoethane | β-Naphthoquinone | Sodium bisulfate | Water |
| 25 | 1,2-Diaminoethane | Lawsone | Rongalit | Water |
| 26 | 1,2-Diaminoethane | o-Benzoquinone | Sodium hydrosulfite | Water:Methanol (80:20) |
| 27 | 1,3-Diamino-2-hydroxpropane | α-Naphthoquinone | Sodium hydrosulfite | Water |
| 28 | Piperazine | p-Benzoquinone | Sodium hydrosulfite | Water |
| 29 | 1,4-Diamino-cyclohexane | p-Benzoquinone | Sodium borohydride | Water:Acetone (80:20) |

TABLE 8

| Condensation product No. | Total conc. of (A) + (B) (wt. %) | (A):(B) (weight ratio) | pH | Reaction temp. (°C.) | Elapsed time till addition of (C) (Hr) | Stirring time (Hr) | Added amount of (C) (wt. %) | Condensation conversion (%) |
|---|---|---|---|---|---|---|---|---|
| 21 | 0.6 | 1:0.5 | 11.5 | R.T. | 10.0 | 0.5 | 16.7 | 95 |
| 22 | 1 | 1:1 | 11.0 | 60° C. | 4.5 | 0.5 | 10.0 | 96 |
| 23 | 1 | 1:2 | 10.4 | 50° C. | 4.5 | 0.5 | 3.0 | 92 |
| 24 | 3 | 1:0.5 | 11.5 | R.T. | 14.0 | 1.0 | 5.0 | 85 |
| 25 | 3 | 1:0.5 | 11.5 | 60° C. | 18.0 | 2.0 | 5.0 | 83 |
| 26 | 3 | 1:0.5 | 11.5 | 50° C. | 18.0 | 2.0 | 3.0 | 96 |
| 27 | 2 | 1:0.5 | 11.5 | R.T. | 19.0 | 1.0 | 3.0 | 90 |
| 28 | 2 | 1:0.5 | 11.5 | R.T. | 14.0 | 1.0 | 3.0 | 82 |
| 29 | 2 | 1:0.5 | 10.0 | R.T. | 15.0 | 5.0 | 3.0 | 76 |

Example 3 (Experiment Nos. 301 to 309)

In each experiment, polymerization was conducted using a stainless steel polymerization vessel with an inner capacity of 1,000 liters and having a stirrer, as described below.

First, a coating liquid as shown in Table 9 (solvent composition, and concentration of condensation product) was prepared using a condensation product and a solvent given in Table 9. The coating liquid was applied to the inner wall, the stirring shaft, the stirring blades and other areas with which a monomer comes into contact of the polymerization vessel. The applied coating liquid was dried by heating at 40° C. for 15 minutes to form a coating, which was then washed with water.

Then, in the polymerization vessel in which the coating was formed as above, polymerization was carried out in the same manner as in Example 1. After the polymerization was over, the produced polymer was taken out and unreacted monomer was recovered out of the polymerization vessel, followed by washing the inside of the polymerization vessel with water and removing the residual resin.

The batch above comprising the operations of polymerization and washing with water, but not including the coating operation, was repeated the number of times shown in Table 10. After the final batch was over, the amount of polymer scale deposited on an area located in the liquid phase and on an area in the vicinity of the interface between the gas and liquid phases in the polymerization vessel, was measured in the same manner as in Example 1.

Also, the polymer obtained in each experiment was measured for the number of fish eyes which appear when the polymer is formed into a sheet, according to the same method as in Example 1.

Further, in order to evaluate initial coloration of a sheet formed from the polymer obtained in each experiment, luminosity index (L) was measured on each specimen in the same manner as in Example 1.

The results of the above measurements are shown in Table 10.

TABLE 9

| | Coating liquid | | |
|---|---|---|---|
| Exp. No. | Condensation product No. | Concentration (wt. %) | Solvent (weight ratio) |
| 301 | 21 | 0.2 | Water:Methanol (90:10) |
| 302 | 22 | 0.2 | Water:Methanol (95:5) |
| 303 | 23 | 0.2 | Water |
| 304 | 24 | 0.2 | Water:Methanol (90:10) |
| 305 | 25 | 0.2 | Water |
| 306 | 26 | 0.2 | Water:Ethanol (90:10) |
| 307 | 27 | 0.1 | Water:Propanol (90:10) |

TABLE 9-continued

| | Coating liquid | | |
|---|---|---|---|
| Exp. No. | Condensation product No. | Concentration (wt. %) | Solvent (weight ratio) |
| 308 | 28 | 0.3 | Water:Isobutanol (90:10) |
| 309 | 29 | 0.5 | Water:Methanol (90:10) |

TABLE 10

| | Repetition number of batch (batches) | Results of polymerization | | | |
|---|---|---|---|---|---|
| | | Polymer scale amount (g/m$^2$) | | Number of fish eyes | Luminosity index (L) |
| Exp. No. | | Liquid phase | Around interface of gas and liquid phases | | |
| 301 | 8 | 0 | 30 | 8 | 73.0 |
| 302 | 8 | 0 | 60 | 15 | 73.0 |
| 303 | 8 | 0 | 85 | 20 | 73.0 |
| 304 | 8 | 0 | 25 | 7 | 73.0 |
| 305 | 8 | 0 | 88 | 23 | 73.0 |
| 306 | 8 | 0 | 66 | 12 | 73.0 |
| 307 | 8 | 0 | 33 | 8 | 73.0 |
| 308 | 8 | 0 | 40 | 9 | 73.0 |
| 309 | 8 | 0 | 110 | 20 | 73.0 |

Example 4 (Experiment Nos. 401–407)

In each experiment, polymerization was conducted using a stainless steel polymerization vessel with an inner capacity of 20 liters and having a stirrer, as described below.

First, a coating liquid as shown in Table 11 (solvent composition, and concentration of condensation product) was prepared using a condensation product and solvent given in Table 11. The coating liquid was applied to the inner wall, the stirring shaft, the stirring blades and other areas with which a monomer comes into contact of the polymerization vessel. The applied coating liquid was dried by heating at 40° C. for 15 minutes to form a coating, which was then washed with water.

Then, in the polymerization vessel in which the coating was formed as above, polymerization was carried out in the same manner as in Example 2. After the polymerization was over, the produced polymer was taken out and unreacted monomer was recovered out of the polymerization vessel, followed by washing the inside of the polymerization vessel with water and removing the residual resin.

The batch above comprising the operations of polymerization and washing with water, but not including the coating operation, was repeated the number of times shown in Table 12. After the final batch was over, the amount of polymer scale deposited on an area located in the liquid phase and on an area in the vicinity of the interface between the gas and liquid phases in the polymerization vessel, was measured in the same manner as in Example 1.

Further, in order to evaluate initial coloration of a sheet formed from the polymer obtained in each experiment, luminosity index (L) was measured on each specimen in the same manner as in Example 2.

The results of the above measurements are shown in

TABLE 11

| Exp. No. | Condensation product No. | Concentration (wt. %) | Solvent (weight ratio) |
|---|---|---|---|
| 401 | 21 | 0.2 | Water:Methanol (90:10) |
| 402 | 22 | 0.2 | Water:Methanol (95:5) |
| 403 | 23 | 0.2 | Water |
| 404 | 24 | 0.2 | Water:Ethanol (95:5) |
| 405 | 26 | 0.3 | Water:Propanol (95:5) |
| 406 | 27 | 0.3 | Water:Isobutanol (95:5) |
| 407 | 29 | 0.2 | Water:Methanol (95:5) |

Coating liquid (header for above)

TABLE 12

| Exp. No. | Repetition number of batch (batches) | Polymer scale amount (g/m²) Liquid phase | Polymer scale amount (g/m²) Around interface of gas and liquid phases | Luminosity index (L) |
|---|---|---|---|---|
| 401 | 5 | 0 | 33 | 85.0 |
| 402 | 5 | 2 | 61 | 85.0 |
| 403 | 5 | 5 | 65 | 85.0 |
| 404 | 5 | 0 | 30 | 85.0 |
| 405 | 5 | 1 | 58 | 85.0 |
| 406 | 5 | 1 | 60 | 85.0 |
| 407 | 5 | 0 | 28 | 85.0 |

We claim:

1. A process of producing a polymer by polymerization of a monomer having an ethylenically unsaturated double bond in a polymerization vessel, comprising the step of carrying out the polymerization in a polymerization vessel having, on its inner wall surface, a coating comprising a condensation product obtained by condensing (A) an aliphatic diamine compound and
(B) a quinone compound in an aqueous medium, whereby polymer scale is prevented from being deposited, wherein said component (A) comprises at least one compound selected from the group consisting of diaminoalkanes of from 2-12 carbon atoms, diaminocycloalkanes of from 3-8 carbon atoms, diaminodialkyl sulfides having the general formula (1)

$$H_2N-C_mH_{2m}-S-C_nH_{2n}NH_2 \qquad (1)$$

wherein m is an integer from 2-12 an n is an integer from 2-12 and piperazine, wherein a reaction stopper (C) is added to components (A) and (B) when the condensation conversion of components (A) and (B) has reached a value in the range of from 70-90% by weight.

2. The process of claim 1, wherein the polymerization is carried out by suspension polymerization, emulsion polymerization, solution polymerization or gas phase polymerization.

3. The process of claim 1, wherein the monomer is selected from the group consisting of vinyl esters; vinyl halides, vinylidene halides; acrylic acid and methacrylic acid and their esters and salts; diene monomers; styrene; acrylonitrile; α-methylstyrene; and vinyl ethers.

4. The process of claim 1, wherein said reaction stopper (C) is sodium hydrosulfite.

5. The process of claim 1, wherein said reaction stopper (C) is sulfur dioxide.

6. The process of claim 1, wherein said reaction stopper (C) is sodium bisulfate.

7. The process of claim 1, wherein said reaction stopper (C) is sodium borohydride.

8. The process of claim 1, wherein said quinone compound is p-benzoquinone.

* * * * *